United States Patent
Demoulin et al.

(10) Patent No.: US 11,234,911 B2
(45) Date of Patent: Feb. 1, 2022

(54) METHOD FOR PRODUCING CAPSULES COMPRISING AT LEAST ONE VOLATILE COMPOUND, AND RESULTING CAPSULES

(71) Applicant: CAPSUM, Marseilles (FR)

(72) Inventors: Damien Demoulin, Paris (FR); Ludivine Mousnier, Villebon-sur-Yvette (FR); Jamie Walters, Paris (FR)

(73) Assignee: CAPSUM, Marseilles (FR)

( * ) Notice: Subject to any disclaimer, the term of this patent is extended or adjusted under 35 U.S.C. 154(b) by 35 days.

(21) Appl. No.: 16/495,843

(22) PCT Filed: Mar. 21, 2018

(86) PCT No.: PCT/EP2018/057213
§ 371 (c)(1),
(2) Date: Sep. 20, 2019

(87) PCT Pub. No.: WO2018/172430
PCT Pub. Date: Sep. 27, 2018

(65) Prior Publication Data
US 2020/0038297 A1 Feb. 6, 2020

(30) Foreign Application Priority Data

Mar. 21, 2017 (FR) ...................... 17 52319

(51) Int. Cl.
*A61K 8/11* (2006.01)
*A61K 8/04* (2006.01)
(52) U.S. Cl.
CPC ............... *A61K 8/11* (2013.01); *A61K 8/042* (2013.01)
(58) Field of Classification Search
CPC ........ A61K 8/11; A61K 2800/56; A61K 8/92; B01J 13/14
See application file for complete search history.

(56) References Cited

FOREIGN PATENT DOCUMENTS

| WO | WO 93/02712 A1 | 2/1993 | |
|---|---|---|---|
| WO | WO 97/22409 A1 | 6/1997 | |
| WO | WO 2005/002719 A1 | 1/2005 | |
| WO | WO 2006/056093 A1 | 6/2006 | |
| WO | WO 2008/064999 A2 | 6/2008 | |
| WO | WO 2008/134908 A1 | 11/2008 | |
| WO | WO-2017046344 A1 * | 3/2017 | ............ B01F 3/0811 |
| WO | WO-2017046360 A1 * | 3/2017 | ............ A01N 25/28 |

OTHER PUBLICATIONS

International Search Report dated Nov. 7, 2018 in International Application No. PCT/EP2018/057213.
Written Opinion in International Application No. PCT/EP2018/057213.
Preliminary Search Report dated Dec. 14, 2017 in related French Patent Application No. 17 52319.

* cited by examiner

*Primary Examiner* — Andrew S Rosenthal
(74) *Attorney, Agent, or Firm* — Pearne & Gordon LLP

(57) ABSTRACT

The present invention relates to a process for preparing solid microcapsules comprising the following steps:
  a) preparation of a composition C1, which is either a composition C1a, comprising a single hydrophobic solid particle, or a composition C1b comprising a plurality of hydrophobic solid particles dispersed in a hydrophilic phase,
  b) addition with stirring of the composition C1 in a polymeric composition C2 at a temperature $T_b$, whereby an emulsion (E1) is obtained;
  c) addition, with stirring, of the emulsion (E1) in a composition C3 at a temperature $T_c$, whereby a double emulsion (E2) is obtained;
  d) applying a shear to the emulsion (E2), whereby a double emulsion (E3) is obtained; and
  e) polymerization of the composition C2, whereby solid microcapsules dispersed in the composition C3 are obtained.

18 Claims, No Drawings

METHOD FOR PRODUCING CAPSULES COMPRISING AT LEAST ONE VOLATILE COMPOUND, AND RESULTING CAPSULES

The subject of the present invention relates to a preparation method for preparing a compound comprising at least one volatile compound. The invention also relates to the capsules obtained as well as compositions, in particular cosmetic compositions, containing the capsules.

Many highly volatile compounds are often present in the formulated products, especially perfuming compounds which give the formulated products interesting odorous properties.

Because of their volatile nature, these compounds evaporate rapidly from the formulated product that contains them, which limits their interest since the formulated product thus rapidly loses its odorous properties.

In addition, some of these compounds are fragile and likely to be degraded as a result of interactions with their environment by mechanisms such as hydrolysis, thermal denaturation or oxidation, which also restricts the life of the odorous properties of the formulated product.

The encapsulation of volatile compounds represents a very interesting way to limit their evaporation and prevent their degradation, thus increasing the lifetime of the odorous performance of the formulated product that contains them.

A very large number of capsules have been developed in order to protect and/or isolate active ingredients in formulated products, and especially volatile compounds. These capsules are the results obtained by manufacturing methods such as spray-drying, interfacial polymerization, interfacial precipitation, or solvent evaporation among many others. The diffusion time of volatile compounds through the capsule-forming materials made through most of these methods remains very short, resulting in very rapid leakage of the capsules. Thus, the life of the odorous properties of the formulated product that contains them is not significantly longer.

The difficulty of providing a truly effective barrier to the diffusion of volatile compounds means that, to date, there is no capsule with satisfactory protection and retention properties of these volatile compounds. In other words, the development of capsules with improved protection and retention properties of volatile compounds remains a constant goal.

The present invention therefore serves the object of providing a method for encapsulating volatile compounds, or even very highly volatile, while also preventing the aforementioned drawbacks.

The present invention therefore also serves the object of providing an encapsulation method by means of double emulsion that makes it possible to obtain size controlled capsules with a size in particular of less than 20 μm, or even 5 μm.

The present invention also serves the object of providing capsules containing at least one volatile compound, or even very highly volatile, that exhibit excellent retention capacity.

The present invention also aims to provide capsules containing at least one volatile, or very volatile, compound limiting the diffusion of chemical species capable of degrading said volatile compounds and thus protect the volatile compounds from degradation.

The present invention also aims to improve the performance of formulated products containing highly volatile compounds by providing capsules having an effective barrier to their evaporation and protection against degradation.

Thus, the present invention concerns a method for preparing solid microcapsules comprising the following steps:
a) the preparation of a composition C1, which is either a composition C1a, comprising a single hydrophobic solid particle, or a composition C1b, comprising a plurality of hydrophobic solid particles dispersed in a hydrophilic phase, wherein the hydrophobic solid particle(s) contain(s) one or more lipophilic volatile compounds and one or more hydrophobic materials, solid at room temperature and liquid at a temperature above $T_m$,
b) the addition, under agitation, of said composition C1 into a polymeric composition C2 at a temperature $T_b$, wherein the compositions C1 and C2 are immiscible with each other;
   the temperature $T_b$ being greater than $T_m$ when the composition C1 is a composition C1a and the temperature $T_b$ being less than $T_m$ when the composition C1 is a composition C1b,
   the composition C2 comprising at least one monomer or polymer, at least one crosslinking agent, and optionally at least one (photo)initiator or a crosslinking catalyst,
   the viscosity of the composition C2 being comprised between 500 mPa·s and 100,000 mPa·s at 25° C., and preferably being greater than the viscosity of the composition C1;
   whereby an emulsion (E1) is obtained comprising droplets of the composition C1a or C1b dispersed in the composition C2;
c) the addition, under agitation, of the emulsion (E1) in a C3 composition at a temperature $T_c$, the compositions C2 and C3 being immiscible with each other; the temperature $T_c$ being greater than $T_m$ when the emulsion (E1) comprises drops of composition C1a dispersed in composition C2, and the temperature $T_m$ being less than $T_m$ when the emulsion (E1) comprises drops of composition C1b dispersed in the composition C2,
   the viscosity of the composition C3 being between 500 mPa·s and 100,000 mPa·s at 25° C., and being greater than the viscosity of the emulsion (E1);
   whereby a double emulsion (E2) is obtained comprising droplets dispersed in the composition C3;
d) the application of a shear to the emulsion (E2), at a temperature $T_d$, the temperature $T_d$ being greater than $T_m$ when the composition C1 of step a) is a composition C1a, and the temperature $T_d$ being less than $T_m$ when the composition C1 of step a) is a composition C1b,
   whereby a double emulsion (E3) is obtained comprising size controlled droplets dispersed in the composition C3; and
e) the polymerisation of the composition C2, whereby solid microcapsules dispersed in the composition C3 are obtained.

The method of the invention therefore makes it possible to prepare solid microcapsules comprising a core and a solid enveloping shell that completely encapsulates at its periphery the core, in which the core is a composition C1 comprising at least one hydrophobic solid particle containing one or more lipophilic volatile compounds.

The capsules of the invention offer excellent retention capacities of volatile compounds that they contain, through several mechanisms to reduce or even eliminate their evaporation:
The core of the capsules contains a material, or a mixture of materials, in which the volatile compounds are soluble. The volatile compounds thus have a high affinity for this material, which greatly limits their volatile character.

When the core of the capsules contains more than one particle, they are dispersed in a hydrophilic phase in which the solubility of the volatile compounds is negligible. This makes it possible to contain the volatile compounds in the particles and to prevent their diffusion towards the outside of the capsules.

The polymer forming the rigid envelope of the capsules advantageously limits the diffusion of the chemical species through this envelope, in particular the diffusion of the volatile compounds towards the outside of the capsules.

The polymer forming the rigid envelope of the capsules also advantageously limits the diffusion (or penetration) of chemical species capable of degrading the volatile compounds through this envelope, thus protecting the volatile compounds from degradation.

The method of the invention consists in producing a double emulsion composed of droplets containing the particles of volatile compounds enveloped in a crosslinkable liquid phase. These double drops are then rendered monodisperse in size before being converted by crosslinking or polymerization in rigid capsules. The preparation involves 5 steps described below in detail.

Step a)

Step a) of the process according to the invention consists in preparing a composition C1 comprising at least one hydrophobic solid particle containing at least one volatile lipophilic compound.

The core of the microcapsules of the invention may be prepared in two different ways depending on whether it is desired that it be composed of one or more particles, i.e. according to the nature of C1 (C1a or C1b).

According to one embodiment, when the composition C1 is a composition C1a, step a) comprises a step of heating the hydrophobic material(s) to a temperature above $T_m$, followed by a step of adding the volatile lipophilic compound(s), and a step of mixing the whole at a temperature above $T_m$.

Thus, if only one particle is desired in the core so as to obtain a composition C1a, the hydrophobic material or the mixture of hydrophobic materials intended to form the particles is heated above $T_m$. The volatile compounds are then added and the mixture formed is stirred while maintaining the temperature above $T_m$.

According to another embodiment, when the composition C1 is a composition C1b, the step a) further comprises a step of dispersing the composition C1a in a hydrophilic phase, while optionally further comprising at least one dispersing agent and/or at least one gelling agent, followed by a step of cooling the dispersion thus obtained to a temperature below $T_m$, whereby hydrophobic solid particles dispersed in said hydrophilic phase are obtained.

Thus, if several particles are desired in the core of the microcapsules, the mixture C1a is dispersed in a hydrophilic phase immiscible with C1a, preferably in the presence of at least one dispersing agent as described below. The emulsion obtained is then cooled below $T_n$, in order to make the particles of volatile compounds solid.

Composition C1

The composition C1 according to the invention comprises at least one hydrophobic solid particle, said particle containing at least one volatile lipophilic compound and at least one hydrophobic material, solid at room temperature and liquid at a temperature greater than $T_m$.

According to one embodiment, the composition C1 comprises a single hydrophobic solid particle. This one is named C1a.

According to another embodiment, the composition C1 comprises a plurality of hydrophobic solid particles which are then dispersed in a hydrophilic phase. Such a composition is named C1b. The composition C1b therefore corresponds to the dispersion of a composition C1a in a hydrophilic phase.

As indicated above, the hydrophobic solid particle(s) according to the invention contain(s) one or more volatile lipophilic compounds and one or more hydrophobic materials which are solid at room temperature and which are liquid at a temperature greater than $T_m$.

Volatile Lipophilic Compound

The composition C1 according to the invention comprises at least one volatile lipophilic compound. It may also comprise a mixture of several volatile compounds.

By "volatile compound" is meant a compound capable of evaporating in less than one hour, at ambient temperature (25° C.) and atmospheric pressure (760 mmHg). A volatile compound according to the invention is therefore liquid at ambient temperature, in particular having a non-zero vapor pressure, at ambient temperature and atmospheric pressure, in particular having a vapor pressure ranging from 0.13 Pa to 40 000 Pa ($10^{-3}$ to 300 mm Hg), and preferably from 1.3 Pa at 13 000 Pa (0.01 to 100 mm Hg), and preferably ranging from 1.3 Pa to 1300 Pa (0.01 to 10 mm Hg). The evaporation rate of a volatile compound according to the invention may be evaluated, in particular, by means of the protocol described in the international application WO2006/013413, and more particularly by means of the protocol described below.

15 g of volatile compound to be tested are introduced into a crystallizer (diameter: 7 cm) placed on a balance in a chamber of about 0.3 m$^3$ regulated in temperature (25° C.) and humidity (relative humidity 50%).

The liquid is allowed to evaporate freely, without stirring, providing ventilation by a fan (PAPST-MOTOREN, reference 8550 N, rotating at 2700 rpm) arranged in a vertical position above the crystallizer containing the compound the blades being directed towards the crystallizer at a distance of 20 cm from the bottom of the crystallizer.

The mass of volatile compound remaining in the crystallizer is measured at regular intervals of time.

The evaporation profile of the volatile compound is then obtained by plotting the curve of the amount of product evaporated (in mg/cm$^2$) as a function of time (in min). Then the evaporation rate that corresponds to the tangent at the origin of the curve obtained is calculated. The evaporation rates are expressed in mg of volatile compound evaporated per unit area (cm$^2$) and per unit of time (minute).

In the context of the present invention, the volatile compounds are lipophilic, and are thus miscible in the hydrophobic material, in particular the waxes/butters, and immiscible in the hydrophilic phase, when present, in which the particles are suspended.

According to one embodiment, the volatile lipophilic compounds are chosen from perfuming agents; flavonoids; polyunsaturated fatty acids; and mixtures thereof, preferably perfuming agents.

According to the invention, the volatile lipophilic compound may be in the form of a mixture. Thus, the volatile lipophilic compound according to the invention may comprise a single perfuming agent (or single perfume) or a mixture of several perfuming agents (or mixture of several perfumes).

Among the perfuming agents, mention may be made of any type of perfume or fragrance, these terms being used here indifferently. These perfumes or fragrances are well known to those skilled in the art and include, in particular, those mentioned, for example, in S. Arctander, Perfume and Flavor Chemicals (Montclair, N J, 1969), S. Arctander, Perfume and Flavor Materials of Natural Origin (Elizabeth, N.J., 1960), in the International Fragrance Association's list (IFRA http://www.ifraorg.org/en/ingredients) and in "Flavor and Fragrance Materials," 1991 (Allured Publishing Co. Wheaton, Ill., USA).

The perfumes used in the context of the present invention may include natural products such as extracts, essential oils, absolutes, resinoids, resins, concretes, etc., as well as basic synthetic substances such as hydrocarbons and alcohols. aldehydes, ketones, ethers, acids, esters, acetals, ketals, nitriles, etc., including saturated and unsaturated compounds, aliphatic, alicyclic and heterocyclic compounds.

According to one embodiment, the perfuming agent comprises less than 10% or even less than 7.5%, by weight of compound(s) with a Clog P less than 2.1, relative to the total weight of said perfuming agent.

According to one embodiment, the perfuming agent does not comprise a compound with a Clog P less than 2.1.

According to one embodiment, the content by weight of volatile compounds is between 50% and 99%, preferably between 70% and 98%, relative to the weight of the composition C1a.

According to one embodiment, when the composition C1 is a composition C1b, the composition C1a represents between 20% and 70% of the weight of C1b. The weight of volatile compounds then represents between 10% and 69.3% of the weight of C1b, preferably between 14% and 68.6%.

According to one embodiment, the core of the capsules (formed by the composition C1a or C1b) represents between 20% and 70% of the weight of the capsules. The weight of volatile compounds thus represents between 10% and 69.3% (preferably between 14% and 68.6%) of the weight of the capsules for capsules whose core is formed by a composition C1a (a single particle), or between 2% and 48.5% (preferably between 2.8% and 48%) of the weight of the capsules for capsules whose core is formed by a composition C1b (dispersion of several particles).

Hydrophobic Material

The hydrophobic particles of the composition C1 according to the invention contain at least one hydrophobic material.

According to one embodiment, said hydrophobic material is a solid compound at room temperature and liquid at a temperature T greater than $T_m$. Preferably, $T_m$ is between 30° C. and 80° C., and preferably between 35° C. and 55° C.

According to one embodiment, the hydrophobic material or materials are chosen from waxes, butters or pasty fatty substances, and mixtures thereof.

Wax(es)

For the purposes of the invention, the term "wax" means a lipophilic compound, solid at room temperature (25° C.), with reversible solid/liquid state change, having a melting point greater than or equal to 30° C. up to 120° C., preferably 80° C.

The protocol for measuring this melting point is described below.

The waxes that may be used according to the invention may be chosen from waxes, solid, deformable or not at room temperature, of animal, vegetable, mineral or synthetic origin, and mixtures thereof.

In particular, it is possible to use hydrocarbon-based waxes such as beeswax, lanolin wax, and Chinese insect waxes; rice wax, Carnauba wax, Candelilla wax, Ouricurry wax, Alfa wax, cork fiber wax, sugar cane wax, Japanese wax and sumac wax; montan wax, microcrystalline waxes, paraffins and ozokerite; polyethylene waxes, waxes obtained by Fisher-Tropsch synthesis and waxy copolymers and their esters.

In particular may be mentioned, polyvinyl ether waxes, waxes based on cetyl palmitate, glycerol ester and fatty acid waxes, ethylene copolymer waxes, oxidized polyethylene waxes, ethylene homopolymer waxes, polyethylene, polyether waxes, ethylene/vinyl acetate copolymer waxes and polypropylene waxes, the waxes sold under the names Kahlwax® 2039 (INCI name: Candelilla cera) and Kahlwax® 6607 (INCI name: *Helianthus Annuus* Seed Wax) by the company Kahl Wachsraffinerie, Casid HSA (INCI name: Hydroxystearic Acid) by SACI CFPA, Performa® 260 (INCI name: Synthetic wax) and Performa® 103 (INCI name: Synthetic wax) by New Phase, and AJK-CE2046 (INCI name: Cetearyl alcohol, dibutyl lauroyl glutamide, dibutylethylhaxanoyl glutamide) by the company Kokyu Alcohol Kogyo.

Mention may also be made of waxes obtained by catalytic hydrogenation of animal or vegetable oils having linear or branched $C_8$-$C_{32}$ fatty chains.

Among these may be mentioned hydrogenated jojoba oil, hydrogenated sunflower oil, hydrogenated castor oil, hydrogenated coconut oil and hydrogenated lanolin oil, di-tetrastearate (trimethylol-1,1,1propane) sold under the name "HEST 2T-4S" by the company HETERENE, di-(1,1,1-trimethylolpropane) tetra-enehenate sold under the name HEST 2T-4B by the company HETERENE.

It is also possible to use the waxes obtained by transesterification and hydrogenation of vegetable oils, such as castor oil or olive oil, such as the waxes sold under the names Phytowax ricin 16L64® and 22L73® and Phytowax Olive 18L57 by the company Sophim. Such waxes are described in application FR-A-2792190.

As wax within the meaning of the invention, mention may also be made of hydrocarbons (n-alkanes, branched alkanes, olefins, cyclic alkanes, isoprenoids), ketones (monocetones, β-diketones), secondary alcohols, alkanediols (alkane-1,2-diols, alkane-2,3-diols, alkane-α, ω-diols), acids (alkenoic acid and alkanoic acid), ester waxes (primary alcohol esters and secondary alcohol esters), the diester waxes (alkanediol diesters, hydroxyl acid diesters), the triesterglycerols, triesters of alkane-1,2-diol, ω-hydroxy acid and of fatty acid, esters of hydroxymalonic acid, fatty acid and alcohol, triesters of hydroxyl acids, fatty acid and fatty alcohol, triesters of fatty acid, hydroxyl acid and diol) and polyester waxes (polyesters of fatty acids). For example, n-octacosan, n-heptacosane, n-hexacosane, n-pentacosan, n-tetracosane, n-tricosane, n-docosan, n-heneicosane and n-eicosane may be mentioned, n-nonadecane, myristyl alcohol, pentadecyl alcohol, cetyl alcohol, palmitoleyl alcohol, heptadecyl alcohol, stearyl alcohol, nonadecyl alcohol, arachidyl alcohol, henicosyl alcohol, behenyl alcohol, erucyl alcohol, lignocyl alcohol, ceryl alcohol, 1-heptacosanol, montanyl alcohol, cluytylic alcohol, 1-octacosanol, 1-nonacosanol, myricylic alcohol, melissyl alcohol, 1-triacontanol and 1-dotriacontanol.

The fatty acids that may be used as waxes in the context of the invention are, for example, cerotic acid, palmitic acid, stearic acid, behenic acid, lignoceric acid, arachidic acid, myristic acid, lauric acid, tridecyclic acid, pentadecyclic acid, margaric acid, nonadecyclic acid, henicosylic acid, tricosylic acid, pentacosylic acid, heptacosylic acid, montanic acid, and nonacosylic acid.

The fatty acid esters which may be used as waxes in the context of the invention are, for example, cetyl palmitate, cetyl octanoate, cetyl laurate, cetyl lactate, cetyl isononanoate, cetyl stearate, stearyl stearate, myristyl stearate, cetyl myristate, isocetyl stearate, glyceryl trimyristate, glyceryl tripalmitate, glyceryl monostearate and glyceryl and cetyl palmitate.

It is also possible to use silicone waxes, which may advantageously be substituted polysiloxanes, preferably at a low melting point.

Among the commercial silicone waxes of this type, mention may be made in particular of those sold under the names Abilwax 9800, 9801 or 9810 (GOLDSCHMIDT), KF910 and KF7002 (SHIN ETSU), or 176-1118-3 and 176-11481 (GENERAL ELECTRIC).

The silicone waxes that may be used may also be alkyl or alkoxydimethicones such as the following commercial products: Abilwax 2428, 2434 and 2440 (GOLDSCHMIDT), or VP 1622 and VP 1621 (WACKER), as well as ($C_{20}$-$C_{60}$) alkyldimethicones, in particular especially ($C_{30}$-$C_{45}$) alkyldimethicones such as the silicone wax sold under the name SF-1642 by the company GE-Bayer Silicones.

It is also possible to use hydrocarbon waxes modified with silicone or fluorinated groups such as, for example, siliconyl candelilla, siliconyl beeswax and Fluorobeeswax by Koster Keunen.

The waxes may also be chosen from fluorinated waxes.

Butter(s) or Pasty Fatty Substance

For the purposes of the present invention, the term "butter" (also referred to as "pasty fatty substance") is understood to mean a lipophilic fatty compound with a reversible solid/liquid state change and comprising at the temperature of 25° C., a liquid fraction and a solid fraction, and at atmospheric pressure (760 mm Hg). In other words, the starting melting temperature of the pasty compound may be less than 25° C. The liquid fraction of the pasty compound measured at 25° C. may represent from 9% to 97% by weight of the compound. This liquid fraction at 25° C. is preferably between 15% and 85%, more preferably between 40% and 85% by weight. Preferably, the one or more butters have an end-of-melting temperature of less than 60° C. Preferably, the one or more butters have a hardness less than or equal to 6 MPa.

Preferably, the butters or pasty fatty substances have in the solid state an anisotropic crystalline organization, visible by X-ray observations.

For the purposes of the invention, the melting temperature corresponds to the temperature of the most endothermic peak observed in thermal analysis (DSC) as described in ISO 11357-3; 1999. The melting point of a paste or a wax may be measured using a differential scanning calorimeter (DSC), for example the calorimeter sold under the name "DSC 02000" by the company TA Instruments.

Concerning the measurement of the melting temperature and the determination of the end-of-melting temperature, the sample preparation and measurement protocols are as follows: A sample of 5 mg of pasty fatty substance (or butter) or wax previously heated to 80° C., and taken with magnetic stirring using an equally heated spatula is placed in an airtight aluminum capsule or crucible. Two tests are carried out to ensure the reproducibility of the results.

The measurements are carried out on the calorimeter mentioned above. The oven is subjected to a nitrogen sweep. The cooling is ensured by the RCS 90 heat exchanger. The sample is then subjected to the following protocol, first being brought to a temperature of 20° C. and then subjected to a first temperature rise ranging from 20° C. to 80° C., at the heating rate of 5° C./minute, then cooled from 80° C. to −80° C. at a cooling rate of 5° C./minute, and finally subjected to a second temperature rise from −80° C. to 80° C. at a heating rate of 5° C./minute. During the second rise in temperature, the variation of the power difference absorbed by the empty crucible and the crucible containing the butter sample is measured as a function of temperature. The melting point of the compound is the value of the temperature corresponding to the peak apex of the curve representing the variation of the difference in power absorbed as a function of the temperature. The end-of-melting temperature corresponds to the temperature at which 95% of the sample melted.

The liquid fraction by weight of the butter (or pasty fatty substance) at 25° C. is equal to the ratio of the heat of fusion consumed at 25° C. relative to the enthalpy of melting of the butter. The enthalpy of melting of the butter or pasty compound is the enthalpy consumed by the compound to pass from the solid state to the liquid state.

The butter is said to be in the solid state when the entirety of its mass is in crystalline solid form. The butter is said to be in the liquid state when the entirety of its mass is in liquid form. The melting enthalpy of the butter is equal to the integral of the whole of the melting curve obtained with the aid of the calorimeter referred to, with a rise in temperature of 5° C. or 10° C. per minute, according to the standard ISO 11357-3: 1999. The melting enthalpy of the butter is the amount of energy required to pass the compound from the solid state to the liquid state. It is expressed in J/g.

The enthalpy of fusion consumed at 25° C. is the amount of energy absorbed by the sample to change from the solid state to the state it has at 25° C. consisting of a liquid fraction and a solid fraction. The liquid fraction of the butter measured at 32° C. preferably represents from 30% to 100% by weight of the compound, preferably from 50% to 100%, more preferably from 60% to 100% by weight of the compound. When the liquid fraction of the butter measured at 32° C. is 100%, the temperature of the end-of-melting range of the pasty compound is less than or equal to 32° C. The liquid fraction of the butter measured at 32° C. is equal to the ratio of the enthalpy of fusion consumed at 32° C. on the enthalpy of melting of the butter. The enthalpy of melting consumed at 32° C. is calculated in the same way as the enthalpy of melting consumed at 23° C.

For hardness measurement, the sample preparation and measurement protocols are as follows: the butter is placed in a 75 mm diameter mold that is about 75% full. In order to overcome the thermal past and control the crystallization, the mold is placed in the Votsch VC0018 programmable oven where it is first heated to 80° C. for 60 minutes, then cooled from 80° C. to 0° C. at a cooling rate of 5° C./minute, then left at the stabilized temperature of 0° C. for 60 minutes, then subjected to a temperature rise from 0° C. to 20° C., at a heating rate of h 5° C./minute, then left at the stabilized temperature of 20° C. for 180 minutes. The compression force measurement is performed with the Swantech TA/TX2i texturometer. The probe used is chosen according to the texture: cylindrical steel probe 2 mm in diameter for very rigid raw materials; cylindrical steel probe 12 mm in diameter for rigid raw materials. The measurement comprises 3 steps: a first step after automatic detection of the surface of the sample where the probe moves at a measuring speed of 0.1 mm/s, and penetrates into the butter at a depth of penetration of 0.3 mm, the software notes the value of the maximum force reached; a second so-called relaxation stage where the probe stays at this position for one second and where the force is noted after 1 second of relaxation; finally a third so-called withdrawal step where the probe returns to its initial position at the speed of 1 mm/s and the energy of withdrawal of the probe (negative force) is recorded.

The value of the hardness measured in the first step corresponds to the maximum compression force measured in Newton divided by the surface area of the texturometer cylinder expressed in $mm^2$ in contact with the butter or emulsion according to the invention. The value of hardness obtained is expressed in mega-pascals or MPa.

The pasty fatty substance or butter may be chosen from synthetic compounds and compounds of plant origin. A pasty fatty substance may be obtained synthetically from starting materials of plant origin.

The pasty fatty substance is advantageously chosen from:
lanolin and its derivatives such as lanolin alcohol, oxyethylenated lanolins, acetylated lanolin, lanolin esters such as isopropyl lanolate, oxypropylenated lanolines,
polymeric or non-polymeric silicone compounds, such as polydimethylsiloxanes of high molecular weight, polydimethylsiloxanes with side chains of the alkyl or alkoxy type having from 8 to 24 carbon atoms, especially stearyl dimethicones,
polymeric or non-polymeric fluorinated compounds,
vinyl polymers, in particular
homopolymers of olefins,
copolymers of olefins,
homopolymers and copolymers of hydrogenated dienes,
linear or branched oligomers, homo or copolymers of alkyl (meth) acrylates, preferably having a $C_8$-$C_{30}$ alkyl group,
homo and copolymeric oligomers of vinyl esters having $C_8$-$C_{30}$ alkyl groups,
homo and copolymer oligomers of vinyl ethers having $C_8$-$C_{30}$ alkyl groups,
liposoluble polyethers resulting from the polyetherification between one or more $C_2$-$C_{100}$, preferably $C_2$-$C_{50}$, diols,
esters and polyesters, and
their mixtures.

According to a preferred embodiment of the invention, the particular butter(s) are of plant origin such as those described in Ullmann's Encyclopedia of Industrial Chemistry ("Fats and Fatty Oils", A. Thomas, published on 15 Jun. 2000, D01: 10.1002/14356007.a10_173, point 13.2.2.2F, Shea Butter, Borneo Tallow, and Related Fats (Vegetable Butters).

More particularly C10-C18 triglycerides (INCI name: C10-18 Triglycerides) comprising at a temperature of 25° C. and at atmospheric pressure (760 mm Hg), a liquid fraction and a solid fraction, shea butter, Nilotica Shea butter (*Butyrospermum parkii*), Galam butter (*Butyrospermum parkii*), Borneo butter or fat or Tengkawang tallow) (*Shorea stenoptera*), Shorea butter, Illipé butter, *Madhuca* butter or Bassia *Madhuca longifolia*, mowrah butter (*Madhuca Latifolia*), Katiau butter (*Madhuca mottleyana*), Phulwara butter (*M. butyracea*), mango butter (*Mangifera indica*), *Murumuru* butter (*Astrocatyum murumuru*), Kokum butter (*Garcinia Indica*), Ucuuba butter (*Virola sebifera*), Tucuma butter, Painya butter (Kpangnan) (*Pentadesma butyracea*), Coffee butter (*Coffea arabica*), Apricot butter (*Prunus Armeniaca*), Macadamia butter (Macadamia Temifolia), butter in grapes (*Vitis vinifera*), avocado butter (*Persea gratissima*), olive butter (*Olea europaea*), sweet almond butter (*Prunus amygdalus dulcis*), cocoa butter (*Theobroma cacao*) and sunflower butter, butter under the INCI name *Astrocaryum Murumuru* Seed Butter, butter under the INCI name *Theobroma Grandiflorum* Seed Butter, and butter under the INCI name *Irvingia Gabonensis* Kernel Butter, jojoba esters (mixture of wax and oil hydrogenated jojoba) (INCI name: Jojoba esters) and ethyl esters of shea butter (INCI name: Shea butter ethyl esters), and mixtures thereof.

According to one embodiment, when the composition C1 is a composition C1a, the content by weight of hydrophobic materials is between 1% and 50%, preferably between 2% and 30%, relative to the composition of the weight C1a.

According to one embodiment, when the composition C1 is a composition C1b, the composition C1a represents between 20% and 70% of the weight of C1b. The content by weight of hydrophobic materials is therefore between 0.2% and 35%, preferably between 0.4% and 21%, relative to the weight of composition C1b.

Hydrophilic Phase

When the composition C1 is a composition C1b, it comprises a hydrophilic phase in which the above-mentioned hydrophobic solid particles are dispersed.

According to one embodiment, the hydrophilic phase of C1b further comprises at least one dispersing agent and/or at least one gelling agent.

For obvious reasons, such dispersing agents and/or gelling agents are water-soluble or hydrophilic.

Preferably, said hydrophilic phase contains:
between 1% and 10%, preferably between 2% and 6%, by weight of one or more gelling agent(s), and
between 1% and 10%, preferably between 1% and 4%, by weight of one or more dispersing agent(s), relative to the total weight of said hydrophilic phase.

Dispersing Agent

The aforementioned hydrophilic phase may further comprise at least one dispersing agent, different from the gelling agent described below, preferably selected from the group consisting of surfactants; polyacrylates; sugar/polysaccharide esters and fatty acid(s), in particular esters of dextrin and fatty acid(s), esters of inulin and fatty acid(s) or esters of glycerol and of fatty acids; polyamides; polyethers and polyesters of silicone; ethoxylated alcohols; and their mixtures.

According to one embodiment, the dispersing agent is a surfactant which may be selected from the group consisting of nonionic surfactants, anionic surfactants, amphoteric or zwitterionic surfactants and mixtures thereof, preferably nonionic surfactants.

As surfactants that may be used in the present invention, those described in EP 1 764 084 may be mentioned.

Preferably, a surfactant that may be used in the present invention is a nonionic surfactant chosen from sorbitan fatty acid esters and their oxyethylenated derivatives, such as sorbitan monostearate (CTFA name: Sorbitan stearate) sold by ICI under the name Span 60, sorbitan monopalmitate (CTFA name: Sorbitan palmitate) sold by ICI under the name Span 40, oxyethylenated sorbitan stearates, palmitates and oleates (CTFA name: Polysorbate) sold by the company ICI under the names Tween, in particular Polysorbate 60 (Tween 60), Polysorbate 65 (Tween 65), Polysorbate 80 (Tween 80).

Gelling Agent

The aforementioned hydrophilic phase may further comprise at least one gelling agent, different from the dispersing agent described above.

The gelling agent contributes to increasing the viscosity of the hydrophilic phase, and therefore of the composition C1b, which advantageously ensures the kinetic stability of the composition C1b, thus preventing the risk of phase shift during the duration of the manufacturing process.

Also, the relatively high viscosity of the composition C1b ensures the stability of the emulsion (E1) obtained at the end of step b).

According to one embodiment, the gelling agent is chosen from branched polymers, preferably having a molecular weight greater than 5,000 g/mol$^{-1}$, polymers with a molecular weight greater than 5,000 g/mol$^{-1}$, and mixtures thereof. These gelling agents are described in more detail below.

According to one embodiment, the gelling agent is a branched polymer, preferably with a molecular weight greater than 5,000 g/mol$^{-1}$, preferably between 10,000 g/mol$^{-1}$ and 500,000 g/mol$^{-1}$, for example between 50 000 g/mol$^{-1}$ and 300,000 g/mol$^{-1}$.

According to one embodiment, the gelling agent is a polymer with a molecular weight of greater than 5000 g/mol$^{-1}$, preferably between 10 000 g/mol$^{-1}$ and 500 000 g/mol$^{-1}$, for example between 50 000 g/mol$^{-1}$ and 300,000 g/mol$^{-1}$.

According to another embodiment, the gelling agent is chosen from cellulose derivatives, polyacrylates, polyurethanes and their derivatives, polyethers and their derivatives, polyacrylamides, polyvinylpyrrolidone (PVP) and its derivatives, polyvinyl alcohol (PVA) and its derivatives, poly(ethylene glycol), poly(propylene glycol) and their derivatives, polysaccharides, protein derivatives, fatty acid salts, glycerol derivatives, glycoluril derivatives and mixtures thereof. These gelling agents are described in more detail below.

Of course, those skilled in the art will choose hydrophilic or water-soluble gelling agents in view of their implementation in the hydrophilic phase. This selection is part of the general knowledge of those skilled in the art.

According to one embodiment, the hydrophilic phase represents between 30% and 80% by weight relative to the weight of C1b. The core of the capsules represents between 20% and 70% of the weight of the capsules. The hydrophilic phase therefore preferably represents between 6% and 56% of the weight of the capsules.

According to one embodiment, the composition C1b comprises from 30% to 80% by weight of hydrophilic phase and from 20% to 70% by weight of hydrophobic particles relative to the total weight of the composition C1b.

Step b)

The step b) of the method according to the invention consists in preparing a first emulsion (E1).

The first emulsion consists of a dispersion of droplets of the composition C1a (respectively C1b) in a polymeric composition C2 that is immiscible with C1a (respectively C1b), created by addition dropwise of C1a (respectively C1b) to C2 under agitation.

During the step b), while taking into account the parameter $T_m$, the composition C1 is at a temperature of between 0° C. and 100° C., preferably between 10° C. and 80° C., and preferably between 15° C. and 60° C. During the step b), the composition C2 is at a temperature of between 0° C. and 100° C., preferably between 10° C. and 80° C., and preferably between 15° C. and 60° C.

Under the conditions of addition in step b), the compositions C1 and C2 are not miscible with each other, which signifies that the amount (by weight) of the composition C1 capable of being solubilised in the composition C2 is less than or equal to 5%, preferably less than 1%, and preferentially less than 0.5%, in relation to the total weight of the composition C2, and that the amount (by weight) of the composition C2 capable of being solubilised in the composition C1 is less than or equal to 5%, preferably less than 1%, and preferentially less than 0.5%, in relation to the total weight of the composition C1.

Thus, when the composition C1 comes into contact with the composition C2 under agitation, the latter is dispersed in the form of droplets, referred to as single droplets.

The composition C2 is agitated in a manner so as to form an emulsion comprising droplets of the composition C1 dispersed in the composition C2. This emulsion is also referred to as "single emulsion" or C1-in-C2 emulsion.

In order to implement the step b), use may be made of any type of agitator usually used to form emulsions, such as, for example, a mechanical agitator with paddles, a static emulsifier, an ultrasonic homogeniser, a membrane homogeniser, a high pressure homogeniser, a colloid mill, a high shear disperser or a high speed homogeniser.

The composition C1 is as defined above.

To obtain capsules containing a single particle, one will choose to add C1a in C2 at a temperature higher than $T_m$. In other words, in this embodiment, the core of the drops of the first emulsion is entirely formed of C1a or of a single hydrophobic solid particle.

To obtain capsules containing several particles, one will choose to add C1b in C2 at a temperature below $T_m$.

Composition C2

The composition C2 is intended for use in forming the future solid enveloping shell of the microcapsules.

The volume fraction of C1 in C2 may vary from 0.1 to 0.7 in order to control the thickness of the enveloping shell of the capsules obtained at the end of the method.

According to this embodiment, the destabilization kinetics of the drops of the emulsion (E1) is significantly slow, which allows the envelope of the microcapsules to be polymerized during step e) before the emulsion is destabilized. The polymerization, once completed, then provides thermodynamic stabilization. Thus, the relatively high viscosity of the composition C2 ensures the stability of the emulsion (E1) obtained at the end of step b).

Preferably, the viscosity of the composition C2 at 25° C. is comprised between 1000 mPa·s and 50,000 mPa·s, preferably between 2000 mPa·s and 25,000 mPa·s, and for example between 3000 mPa·s and 15,000 mPa·s.

Preferably, the viscosity of the composition C2 is greater than the viscosity of the composition C1.

The viscosity is measured by means of a rheometer, model Haake Rheostress™ 600 equipped with a cone having 60 mm diameter and 2 degrees cone angle, and a temperature control cell set at 25° C. The value of the viscosity is read for a shear rate of 10 s$^{-1}$.

Preferably, the interfacial tension between the compositions C1 and C2 is low. Typically, these interfacial tensions vary between 0 mN/m and 50 mN/m, preferably between 0 mN/m and 20 mN/m.

The low interfacial tension between the compositions C1 and C2 also advantageously makes it possible to ensure the stability of the emulsion (E1) obtained at the conclusion of step b).

According to one embodiment, the ratio between the volume of composition C1 and the volume of composition C2 varies between 1:10 and 10:1. Preferably, this ratio is between 1:3 and 5:1, preferably between 1:3 and 3:1. This ratio may be adapted to control the thickness of the envelope of the polymerized microcapsules.

The composition C2 contains at least one monomer or polymer, at least one crosslinking agent, and optionally at least one (photo)initiator, or crosslinking catalyst, thereby making it crosslinkable.

According to one embodiment, the composition C2 comprises from 50% to 99% by weight of monomer or polymer, or a mixture of monomers or polymers relative to the total weight of the composition C2.

According to one embodiment, the composition C2 comprises from 1% to 20% by weight of crosslinking agent or of a mixture of crosslinking agents, in relation to the total weight of the composition C2.

According to one embodiment, the composition C2 comprises from 0.1% to 5% by weight of photoinitiator or a mixture of photoinitiators, in relation to the total weight of the composition C2.

According to one embodiment, the composition C2 comprises from 0.001% to 70% by weight, in particular from 0.1% to 50% by weight, of crosslinking agent in relation to the weight of the said composition C2.

According to the invention, the term "monomer" or "polymer" refers to any base unit that is suitable for the formation of a solid material by polymerisation, either alone or in combination with other monomers or polymers.

These monomers may be selected from among monomers comprising at least one reactive functional group selected from among the group constituted of the functions: acrylate, methacrylate, vinyl ether, N-vinyl ether, mercaptoester, thiolene, siloxane, epoxy, oxetane, urethane, isocyanate, and peroxide.

In particular, the monomers may be selected from among monomers bearing at least one of the aforementioned reactive functional groups and in addition bearing at least one functional group selected from among the group constituted of primary-, secondary- and tertiary alkylamine functional groups, quaternary amine functional groups, sulfate-, sulfonate-, phosphate-, phosphonate-, carboxylate-, hydroxyl-, halogen functional groups, and mixtures thereof.

The polymers used in the composition C2 may be selected from among polyethers, polyesters, polyurethanes, polyureas, polyethylene glycols, polypropylene glycols, polyamides, polyacetals, polyimides, polyolefins, polysulphides and polydimethylsiloxanes, the said polymers in addition bearing at least one reactive functional group selected from among the group constituted of the functions: acrylate, methacrylate, vinyl ether, N-vinyl ether, mercaptoester, thiolene, siloxane, epoxy, oxetane, urethane, isocyanate, and peroxide, and mixtures thereof.

Mention of examples of such polymers include, but are not limited to, the following polymers: poly(2-(1-naphthyloxy) ethyl acrylate), poly(2-(2-naphthyloxy) ethyl acrylate), poly(2-(2-naphthyloxy) ethyl methacrylate), polysorbitol dimethacrylate, polyacrylamide, poly((2-(1-naphthyloxy) ethanol), poly(2-(2-naphthyloxy) ethanol), poly(1-chloro-2,3-epoxypropane), poly(n-butyl isocyanate), poly(N-vinyl carbazole), poly(N-vinyl pyrrolidone), poly(p-benzamide), poly(p-chlorostyrene), poly(p-methyl styrene) poly(p-phenylene oxide), poly(p-phenylene sulfide), poly(N-(methacryloxyethyl) succinimide), polybenzimidazole, polybutadiene, polybutylene terephthalate, polychloral, polychloro trifluoro ethylene, polyether imide, polyether ketone, polyether sulfone, polyhydridosilsesquioxane, poly(m-phenylene isophthalamide), poly(methyl 2-acrylamido-2-methoxyacetate), poly(2-acrylamido-2-methylpropane-sulfonic acid), poly-mono-butyl maleate, polybutyl methacrylate, poly(N-tert-butylmethacrylamide), poly(N-n-butylmethacrylamide), polycyclohexylmethacrylamide, poly(m-xylenebisacrylamide 2,3-dimethyl-1,3-butadiene, N,N-dimethylmethacrylamide), poly(n-butyl methacrylate), poly(cyclohexyl methacrylate), polyisobutyl methacrylate, poly(4-cyclohexylstyrene), polycyclol acrylate, polycyclol methacrylate, polydiethyl ethoxymethylenemalonate, poly(2,2,2-trifluoroethyl methacrylate), poly(1,1,1-trimethylol-propane trimethacrylate), polymethacrylate, poly(N,N-dimethylaniline dihydrazide), poly(isophthalic dihydrazine), isophthalic polyacid, polydimethyl benzilketal, epichlorohydrin, poly(ethyl-3,3-diethoxyacrylate), poly(ethyl-3,3-dimethylacrylate), poly(ethyl vinyl ketone), poly(vinyl ethyl ketone), poly(penten-3-one), polyformaldehyde, poly(diallyl acetal), polyfumaronitrile, polyglyceryl propoxy triacrylate, polyglyceryl trimethacrylate, polyglycidoxypropyltrimethoxysilane, polyglycidyl acrylate, poly(n-heptyl acrylate), poly(acrylic acid n-heptyl ester), poly(n-heptyl methacrylate), poly(3-hydroxypropionitrile), poly(2-hydroxypropyl acrylate), poly(2-hydroxypropyl methacrylate), poly(N-(methacryloxyethyl) phthalimide), poly(1,9-nonanediol diacrylate), poly(1,9-nonanediol dimethacrylate), poly(N-(n-propyl) acrylamide), poly(ortho-phthalic acid), poly(iso-phthalic acid), poly(1,4-benzenedicarboxylic acid), poly(1,3-benzenedicarboxylic acid), poly(phthalic acid), poly(mono-2-acryloxyethyl ester), terephthalic polyacid, phthalic polyanhydride, polyethylene glycol diacrylate, polyethylene glycol methacrylate, polyethylene glycol dimethacrylate, poly(isopropyl acrylate), polysorbitol pentaacrylate, polyvinyl bromoacetate, polychloroprene, poly(di-n-hexyl silylene), poly(di-n-propyl siloxane), polydimethyl silylene, polydiphenyl siloxane, polyvinyl propionate, polyvinyl triacetoxysilane, polyvinyl tris-tert-butoxysilane, polyvinyl butyral, polyvinyl alcohol, polyvinyl acetate, polyethylene co-vinyl acetate, poly(bisphenol-A polysulfone), poly(1,3-dioxepane), poly(1,3-dioxolane), poly(1,4-phenylene vinylene), poly(2,6-dimethyl-1A-phenylene oxide), poly(4-hydroxybenzoic acid), poly(4-methyl pentene-1), poly(4-vinylpyridine), polymethylacrylonitrile, polymethylphenylsiloxane, polymethylsilmethylene, polymethylsilsesquioxane, poly(phenylsilsesquioxane) poly(pyromellitimide-1,4-diphenyl ether), polytetrahydrofuran, polythiophene, poly(trimethylene oxide), polyacrylonitrile, polyether sulfone, polyethylene-co-vinyl acetate, poly(perfluoroethylene propylene), poly(perfluoroalkoxy alkane), or poly(styrene)acrylonitrile), and mixtures thereof.

Advantageously, the composition C2 comprises at least one monomer or polymer of cosmetic grade. Advantageously, the composition C2 comprises at least one biodegradable monomer or polymer. A biodegradable monomer or polymer may, in particular, be chosen from CN2035 and/or CN2203 (polyester acrylate oligomer) marketed by Sartomer.

The term "crosslinking agent" is used to refer to a compound bearing at least two reactive functional groups that are capable of crosslinking a monomer or a polymer, or a mixture of monomers or polymers, during its polymerisation.

The crosslinking agent may be selected from among molecules bearing at least two functional groups selected from among the group constituted of the functions: acrylate, methacrylate, vinyl ether, N-vinyl ether, mercaptoester, thiolene, siloxane, epoxy, oxetane, urethane, isocyanate, and peroxide, and mixtures thereof.

By way of crosslinking agent, mention may be made in particular of:
  diacrylates, such as 1,6-hexanediol diacrylate, 1,6-hexanediol dimethacrylate, polyethylene glycol dimethacrylate, 1,9-nonanediol dimethacrylate, 1,4-butanediol dimethacrylate, 2,2-bis(4-methacryloxyphenyl) propane, 1,3-butanediol dimethacrylate, 1,10-decanediol dimethacrylate, bis(2-methacryloxyethyl) N,N'-1,9-nonylene biscarbamate, 1,4-butanediol diacrylate, ethylene glycol diacrylate, 1,5-pentanediol dimethacrylate, 1,4-phenylene diacrylate, allyl methacrylate, N,N'-methylenebisacrylamide, 2,2-bis[4-(2-hydroxy-3-methacryloxypropoxy) phenyl]propane, tetraethylene glycol diacrylate, ethylene glycol dimethacrylate, diethylene glycol diacrylate, triethylene glycol diacrylate, triethylene glycol dimethacrylate, polyethylene glycol diglycidyl ether, N,N-diallylacrylamide, 2,2-bis [4-(2-acryloxyethoxy)phenyl]propane, glycidyl methacrylate;

multifunctional acrylates such as dipentaerythritol pentaacrylate, 1,1,1-trimethylolpropane triacrylate, 1,1,1-trimethylolpropane trimethacrylate, ethylenediamine tetramethacrylate, pentaerythritol triacrylate, pentaerythritol tetraacrylate;

acrylates also having other reactive functional groups, such as propargyl methacrylate, 2-cyanoethyl acrylate, tricyclodecane dimethanol diacrylate, hydroxypropyl methacrylate, N-acryloxysuccinimide, N-(2-hydroxypropyl) methacrylamide, N-(3 aminopropyl) methacrylamide hydrochloride, N-(t-BOC-aminopropyl)methacrylamide, 2-aminoethyl methacrylate hydrochloride, monoacryloxyethyl phosphate, o-nitrobenzyl methacrylate, acrylic anhydride, 2-(tert-butylamino) ethyl methacrylate N,N-diallylacrylamide, glycidyl methacrylate, 2-hydroxyethyl acrylate, 4-(2-acryloxyaheoxy)-2-hydroxybenzophenone, N-(Phthalimidomethyl) acrylamide, cinnamyl methacrylate; and mixtures thereof.

The term "photoinitiator" is used to refer to a compound that is capable of fragmenting under the effect of light radiation.

The photoinitiators which may be used according to the present invention are known in the state of the art and are described, for example in "Les photoinitiateurs dans la réticulation des revetements [Photoinitiators in the crosslinking of coatings]", G. Li Bassi, Double Liaison—Chimie des Peintures [Double Bond—Chemistry of Paints], no 361, November 1985, p. 34-41; "Applications industrielles de la polymérisation photoinduite [Industrial applications of photoinduced polymerisation]", Henri Strub, L'Actualité Chimique [Chemical News], February 2000, p. 5-13; and "Photopolymeres: considérations théoriques et réaction de prise [Photopolymers: theoretical considerations and setting reaction", Marc, J M Abadie, Double Liaison—Chimie des Peintures [Double Bond—Chemistry of Paints], no 435-436, 1992, p. 28-34.

These photoinitiators include:
α-hydroxyketones, such as 2-hydroxy-2-methyl-1-phenyl-1-propanone, marketed for example under the trade names DAROCUR® 1173 and 4265, IRGACURE® 184, 2959, and 500, by the company BASF, and ADDITOL® CPK by the company CYTEC;

α-amino ketones, in particular 2-benzyl-2-dimethylamino-1-(4-morpholinophenyl)-butanone-1, marketed, for example, under the trade names IRGACURE® 907 and 369 by the company BASF;

aromatic ketones marketed for example under the trade name ESACURE® TZT by LAMBERTI; or even thioxanthones marketed for example under the trade name ESACURE® ITX by LAMBERTI, and quinones. These aromatic ketones most often require the presence of a hydrogen donor compound such as tertiary amines and in particular alkanolamines. In particular mention may be made of the tertiary amine ESACURE® EDB marketed by the company LAMBERTI.

α-dicarbonyl derivatives of which the most common representative is benzyldimethylketal marketed under the trade name IRGACURE® 651 by the company BASF. Other commercially available products are marketed by the company LAMBERTI under the trade name ESACURE® KB1, acylphosphine oxides, such as, for example, bis-acylphosphine oxides (BAPO) marketed for example under the trade names IRGACURE® 819, 1700, and 1800, DAROCUR® 4265, LUCIRIN® TPO, and LUCIRIN® TPO-L by the company BASF, and mixtures thereof.

Among the photoinitiators, mention may also be made of aromatic ketones such as benzophenone, phenylglyoxylates, such as the methyl ester of phenylglyoxylic acid, oxime esters, such as [1-(4-phenylsulfanylbenzoyl) heptylideneamino] benzoate, sulphonium salts, iodonium salts and oxime sulphonates, and mixtures thereof.

The catalyst may be chosen from among organic, metal, organometallic or inorganometallic catalysts, and mixtures thereof. As a catalyst may be mentioned organometallic or inorganometallic complexes of platinum, palladium, titanium, molybdenum, copper, zinc, and mixtures thereof.

According to one embodiment, the composition C2 may further comprise an additional monomer or polymer capable of improving the properties of the enveloping shell of the microcapsules and/or of contributing new properties to the enveloping shell of the microcapsules.

Among these additional monomers or polymers, mention may be made of monomers or polymers bearing a group that is sensitive to pH, temperature, UV or IR.

These additional monomers or polymers are able to induce the rupture of the solid microcapsules and as a result the subsequent release of their contents, after stimulation via pH, temperature, UV or IR.

These additional monomers or polymers may be selected from among monomers or polymers bearing at least one reactive functional group selected from among the group constituted of the functions: acrylate, methacrylate, vinyl ether, N-vinyl ether, mercaptoester, thiolene, siloxane, epoxy, oxetane, urethane, isocyanate and peroxide, and also bearing one of the following groups:

a hydrophobic group such as a fluorinated group, for example trifluoroethyl methacrylate, trifluoroethyl acrylate, tetrafluoropropyl methacrylate, pentafluoropropyl acrylate, hexafluorobutyl acrylate, or fluorophenyl isocyanate;

a pH sensitive group such as primary, secondary or tertiary amines, carboxylic acids, phosphate groups, sulfate groups, nitrate groups, or carbonate groups;

a UV-sensitive or UV-cleavable group (or photochromic group) such as azobenzene, spiropyran, 2-diazo-1,2-naphthoquinone, o-nitrobenzyl, thiol, or 6-nitro-veratroyloxycarbonyl, for example poly(ethylene oxide)-block-poly(2-nitrobenzylmethacrylate), and other block copolymers, as described in particular in Liu et al., Polymer Chemistry 2013, 4, 3431-3443;

an IR-sensitive or IR-cleavable group such as o-nitrobenzyl or 2-diazo-1,2-naphthoquinone, for example the polymers described in Liu et al., Polymer Chemistry 2013, 4, 3431-3443; and a temperature sensitive group such as poly (N-isopropylacrylamide).

In the light of the present description, those skilled in the art will be able to adjust the nature and/or the amount of monomer(s) or polymer(s), crosslinking agent(s) and photoinitiator(s) or crosslinking catalyst(s), especially with respect to the desired properties of the solid shell and/or the polymerization step e).

Step c)

The step c) of the method according to the invention consists in preparing a second emulsion (E2).

The second emulsion consists of a dispersion of droplets of the first emulsion in a composition C3 that is immiscible with C2, created by addition dropwise of the first emulsion into C3 under agitation.

As indicated above, to obtain capsules containing a single particle (when the composition C1 is a composition C1a), the preparation of the second emulsion is carried out at a temperature above $T_m$. To obtain capsules containing several particles (when the composition C1 is a composition C1b), the preparation of the second emulsion is carried out at a temperature below $T_m$.

Under the addition conditions of step c), the compositions C2 and C3 are not miscible with each other, which signifies that the amount (by weight) of the composition C2 capable of being solubilised in the composition C3 is less than or equal to 5%, preferably less than 1%, and preferentially less than 0.5%, in relation to the total weight of the composition C3, and that the amount (by weight) of the composition C3 capable of being solubilised in the composition C2 is less than or equal to 5%, preferably less than 1%, and preferentially less than 0.5%, in relation to the total weight of the composition C2.

Thus, when the emulsion (E1) comes into contact with the composition C3 under agitation, the latter is dispersed in the form of droplets, referred to as double droplets, the dispersion of these droplets of emulsion (E1) in the continuous phase C3 being referred to as emulsion (E2).

Typically, a double droplet formed during the step c) corresponds to a single droplet of the composition C1 as described here above, encased by an enveloping shell of composition C2 which completely encapsulates the said single droplet.

The double droplet formed during the step c) may also comprise at least two single droplets of the composition C1, the said single droplets being encased by an enveloping shell of composition C2 which completely encapsulates the said single droplets.

Thus, the said double droplets comprise a core constituted of one or more single droplets of the composition C1, and a layer of the composition C2 encasing the said core.

The resulting emulsion (E2) is generally a polydisperse double emulsion (C1-in-C2-in-C3 emulsion or C1/C2/C3 emulsion), which signifies that the double droplets do not have a clear size distribution in the emulsion (E2).

The immiscibility between the compositions C2 and C3 provides the ability to prevent mixing between the layer of the composition C2 and the composition C3 and thus ensures the stability of the emulsion (E2).

The immiscibility between the compositions C2 and C3 also provides the ability to prevent the volatile compound of the composition C1 from migrating from the core of the droplets to the composition C3.

In order to implement the step c), use may be made of any type of agitator usually used to form emulsions, such as, for example, a mechanical agitator with paddles, a static emulsifier, an ultrasonic homogeniser, a membrane homogeniser, a high pressure homogeniser, a colloid mill, a high shear disperser or a high speed homogeniser.

Composition C3

According to one embodiment, the viscosity of the composition C3 at 25° C. is greater than the viscosity of the emulsion (E1) at 25° C.

According to the invention, the viscosity of the composition C3 at 25° C. is comprised between 500 mPa·s and 100,000 mPa·s.

Preferably, the viscosity of the composition C3 at 25° C. is comprised between 3,000 mPa·s and 100,000 mPa·s, preferentially between 5,000 mPa·s and 80,000 mPa·s, for example between 7,000 mPa·s and 70,000 mPa·s, in particular between 1,000 mPa·s, and more preferably between 5,000 mPa·s and 25,000 mPa·s.

According to this embodiment, given the very high viscosity of the continuous phase formed by the composition C3, the rate of destabilisation of the double droplets of the emulsion (E2) is significantly slow in relation to the duration of the method of the invention, which thus then provides for kinetic stabilisation of the emulsions (E2) and then (E3) until such time as the polymerisation of the enveloping shell of the capsules is completed. The capsules once polymerised are thermodynamically stable.

Thus, the very high viscosity of the composition C3 ensures the stability of the emulsion (E2) obtained at the conclusion of step c).

A high viscosity of the system make it possible to advantageously ensure the kinetic stability of the double emulsion (E2), thus preventing it from undergoing phase separation (dephasing) over the duration of the manufacturing method.

Preferably, the interfacial tension between the compositions C2 and C3 is low. The low interfacial tension between the compositions C2 and C3 also advantageously makes it possible to ensure the stability of the emulsion (E2) obtained at the conclusion of the step c).

The volume fraction of the first emulsion (E1) in C3 can be varied from 0.05 to 0.5 in order, on the one hand, to control the production yield and, on the other hand, to cause to vary the mean diameter of the capsules. At the end of this step, the size distribution of the second emulsion is relatively wide.

According to one embodiment, the ratio between the volume of emulsion (E1) and the volume of composition C3 varies between 1:10 and 10:1. Preferably, this ratio is comprised between 1:9 and 3:1, preferentially between 1:9 and 1:1.

According to one embodiment, the composition C3 is a hydrophobic or hydrophilic phase, preferably a hydrophilic phase.

According to one embodiment, the composition C3 may further comprise at least one gelling agent as described above.

In particular, the composition C3 further comprises at least one branched polymer, preferably with a molecular weight greater than 5000 g/mol$^{-1}$, and/or at least one polymer with a molecular weight greater than 5000 g/mol$^{-1}$, and/or solid particles such as silicates.

According to one embodiment, the composition C3 comprises at least one plugged polymer that may be used as a gelling agent, preferably with a molecular weight greater than 5,000 g/mol$^{-1}$, preferably between 10,000 g/mol$^{-1}$ and 500,000 g/mol$^{-1}$, for example between 50,000 g/mol$^{-1}$ and 300,000 g/mol$^{-1}$.

The term "branched polymer" (or comb polymer) is used to refer to a polymer having at least one branch point between its two end groups, a branch point being a point of a chain on which is attached a side chain also referred to as branch or pendant chain.

Among the branched polymers, mention may be made for example of graft polymers, comb polymers, or indeed star polymers or dendrimers.

According to one embodiment, the composition C3 comprises at least one polymer having a molecular weight greater than 5000 g·mol$^{-1}$, which may be iused as a gelling agent preferentially between 10,000 g/mol$^{-1}$ and 500,000 g/mol$^{-1}$, for example between 50,000 g/mol$^{-1}$ and 300,000 g/mol$^{-1}$.

By way of a polymer that may be used as a gelling agent in the composition C3, mention may be made of the following compounds, used alone or indeed mixed together:
- cellulose and cellulose derivatives, such as cellulose ethers: methyl cellulose, ethyl cellulose, hydroxyethyl cellulose, methylhydroxyethyl cellulose, ethylhydroxyethyl cellulose, carboxymethyl cellulose, hydroxypropyl cellulose, or methylhydroxypropyl cellulose;
- polyacrylates (also known as carbomers), such as polyacrylic acid (PAA), polymethacrylic acid (PMAA), poly(hydroxyethyl methacrylate) (pHEMA), poly(N-2-hydroxypropyl methacrylate) (pHPMA);
- polyacrylamides such as poly(N-isopropylacrylamide) (PNIPAM); polyvinylpyrrolidone (PVP) and the derivatives thereof;
- polyvinyl alcohol (PVA) and the derivatives thereof;
- poly(ethylene glycol), poly(propylene glycol) and the derivatives thereof, such as poly(ethylene glycol) acrylate/methacrylate, poly(ethylene glycol) diacrylate/dimethacrylate, polypropylene carbonate, Aculyn 44 (INCI: PEG-150/Decyl Alcohol/SMDI Copolymer);
- polysaccharides such as carrageenans, alginates, carob gums or tara gums, dextran, xanthan gums, chitosan, agarose, gelatin, agar-agar, hyaluronic acids, gellan gum, guar gum, arabic gum, tragacanth gum, diuretic gum, oat gum, karaya gum, ghatti gum, curdlan gum, pectin, konjac gum, starch, alcasealan (INCI: Alcaligenes Polysaccharides);
- protein derivatives such as gelatin, collagen, fibrin, polylysine, albumin, casein;
- silicone derivatives such as polydimethylsiloxane (also known as dimethicone), alkyl silicones, aryl silicones, alkyl aryl silicones, polyethylene glycol dimethicones, polypropylene glycol dimethicone;
- waxes, such as diester waxes (alkanediol diesters, hydroxyl acid diesters), triester waxes (triacylglycerols; triesters of alkane-1,2-diol, ω-hydroxy acid and fatty acid; esters of hydroxymalonic acid, fatty acid and alcohol; triesters of hydroxyl acids, fatty acid and fatty alcohol, triesters of fatty acid, hydroxyl acid and diol) and polyester waxes (polyesters of fatty acids). The fatty acid esters which may be used by way of waxes in the context of the invention are, for example, cetyl palmitate, cetyl octanoate, cetyl laurate, cetyl lactate, cetyl isononanoate, and cetyl stearate, stearyl stearate, myristyl stearate, cetyl myristate, isocetyl stearate, glyceryl trimyristate, glyceryl tripalmitate, glyceryl monostearate, or glyceryl palmitate and cetyl palmitate;
- fatty acids which may be used as waxes such as cerotic acid, palmitic acid, stearic acid, dihydroxystearic acid, behenic acid, lignoceric acid, arachidic acid, myristic acid, lauric acid, tridecyclic acid, pentadecyclic acid, margaric acid, nonadecyclic acid, henicosylic acid, tricosylic acid, pentacosylic acid, heptacosylic acid, montanic acid or nonacosylic acid;
- fatty acid salts, in particular fatty acid aluminum salts such as aluminum stearate, hydroxyl aluminum bis (2-ethylhexanoate);
- isomerised jojoba oil;
- hydrogenated sunflower oil;
- hydrogenated coconut oil;
- hydrogenated lanolin oil;
- castor oil and the derivatives thereof, in particular modified hydrogenated castor oil or compounds obtained by esterification of castor oil with fatty alcohols;
- polyurethanes and the derivatives thereof;
- styrenic polymers such as styrene butadiene;
- polyolefins such as polyisobutene and
- mixtures thereof.

According to one embodiment, the composition C3 comprises solid particles such as clays, silicas and silicates which may be used as a gelling agent.

By way of solid particles that may be used as a gelling agent, mention may be made of clays and silicates belonging in particular to the category of phyllosilicates (also known as layered silicates). By way of example of a silicate that may be used in the context of the invention, mention may be made of Bentonite, Hectorite, Attapulgite, Sepiolite, Montmorillonite, Saponite, Sauconite, Nontronite, Kaolinite, Talc, Sepiolite, Chalk. The fumed synthetic silicas may also be used. The clays, silicates and silicas previously mentioned above can advantageously be modified by organic molecules such as polyethers, ethoxylated amides, quaternary ammonium salts, long-chain diamines, long-chain esters, polyethylene glycols, polypropylene glycols.

These particles may be used either alone or mixed together.

According to one embodiment, the composition C3 comprises at least one polymer having a molecular weight greater than 5000 g/mol$^{-1}$ and solid particles. Any mixture of the compounds previously mentioned above may be used.

According to a particular embodiment, the composition C3 may itself be a single or multiple emulsion, in which the dispersed phase is independent of the capsules described in the present application and may be stabilized by any means known to those skilled in the art, in particular by means of surfactant(s) or by the formation of a membrane, in particular resulting from an interfacial complex coacervation reaction between a first anionic polymer (especially a carbomer) and a second cationic polymer (in particular an amodimethicone).

Step d)

The step d) of the method according to the invention consists in refining the size of the droplets of the second emulsion (E2).

To obtain capsules containing a single particle (when the composition C1 is a composition C1a), the refining in size is carried out at a temperature above $T_m$. The second monodisperse emulsion is then allowed to cool down to a lower temperature than $T_m$.

To obtain capsules containing several particles (when the composition C1 is a composition C1 b), the size refining is carried out at a temperature below $T_m$.

Step d) may consist in applying a homogeneous controlled shear to the emulsion (E2), with the said shear rate applied comprised between 10 s$^{-1}$ and 100,000 s$^{-1}$.

According to one embodiment, the polydisperse double droplets obtained in the step c) are subjected to a size refinement process consisting of subjecting them to shearing capable of fragmenting them into new double droplets of homogeneous and controlled diameters. Preferably, this fragmentation step is carried out by using a high-shear cell such as the Couette type cell according to a method described in patent application EP 15 306 428.2.

According to one embodiment, in the step d), the second emulsion (E2), obtained at the conclusion of the step c), consisting of polydisperse double droplets dispersed in a continuous phase, is subjected to a shear in a mixer, which applies a homogeneous controlled shear.

Thus, according to this embodiment, the step d) consists in applying a homogeneous controlled shear to the emulsion (E2), with the said shear rate applied comprised between 1000 s$^{-1}$ and 100,000 s$^{-1}$.

According to this embodiment, in a mixer, the shear rate is said to be controlled and homogeneous, regardless of the duration of application, when it passes to a maximum value that is identical for all the parts of the emulsion, at a given time instant that may vary from one point of the emulsion to another. According to the invention, the exact configuration of the mixer is not critical as long as the entire emulsion has been subjected to the same maximum shear when exiting from this device. The mixers that are suitable for carrying out the step d) are described in particular in the document U.S. Pat. No. 5,938,581.

The second emulsion may undergo homogeneous controlled shear when it circulates through a cell formed by:
two concentric rotary cylinders (also referred to as a Couette type mixer);
two parallel rotating discs; or
two parallel oscillating plates.

According to this embodiment, the shear rate applied to the second emulsion is comprised between 1,000 s$^{-1}$ and 100,000 s$^{-1}$, preferably between 1,000 s$^{-1}$ and 50,000 s$^{-1}$, and preferentially between 2,000 s$^{-1}$ and 20,000 s$^{-1}$.

According to this embodiment, during the step d), the second emulsion is introduced into the mixer and is then subjected to shear which results in the formation of the third emulsion. The third emulsion (E3) is chemically identical to the second emulsion (E2) but consists of monodisperse double droplets while the emulsion (E2) consists of polydisperse double droplets. The third emulsion (E3) typically consists of a dispersion of double droplets comprising a core constituted of one or more droplets of the composition C1 and a layer of the composition C2 encapsulating the said core, the said double droplets being dispersed in the composition C3.

The difference between the second emulsion and the third emulsion is the size variance of the double droplets: the droplets of the second emulsion are polydisperse in size while the droplets of the third emulsion are monodisperse, thanks to the fragmentation mechanism described here above.

Preferably, according to this embodiment, the second emulsion is introduced in a continuous manner into the mixer, which signifies that the quantity of double emulsion (E2) introduced at the inlet of the mixer is the same as the quantity of third emulsion (E3) at the outlet of the mixer.

Given that the size of the droplets of the emulsion (E3) corresponds essentially to the size of the droplets of the solid microcapsules after polymerisation, it is possible to adjust the size of the microcapsules and the thickness of the enveloping shell by adjusting the shear rate during the step d), with a strong correlation between the decrease in the size of droplets and the increase in shear rate. This makes it possible to adjust the resulting dimensions of the microcapsules by varying the shear rate applied during the step d).

According to one preferred embodiment, the mixer implemented during the step d) is a Couette type mixer, comprising two concentric cylinders, one external cylinder having internal radius $R_0$, and an internal cylinder having external radius $R_i$, the external cylinder being fixed and the internal cylinder being in rotation with angular velocity ω.

A Couette-type mixer that is appropriate for the method of the invention may be supplied by the company T.S.R. France.

According to one embodiment, the angular velocity ω of the internal rotating cylinder of the Couette type mixer is greater than or equal to 30 rad·s$^{-1}$.

For example, the angular velocity ω of the internal rotating cylinder of the Couette type mixer is about 70 rad·s$^{-1}$.

The dimensions of the fixed external cylinder of the Couette type mixer may be chosen so as to modulate the space $(d=R_o-R_i)$ between the rotating internal cylinder and the fixed external cylinder.

According to one embodiment, the space $(d=R_o-R_i)$ between the two concentric cylinders of the Couette type mixer is comprised between 50 μm and 1000 μm, preferably between 100 μm and 500 μm, for example between 200 μm and 400 μm.

For example, the distance d between the two concentric cylinders is equal to 100 μm.

According to this embodiment, implementing a Couette type mixer, during the step d), the second emulsion is introduced at the inlet of the mixer, typically via a pump, and is directed towards the space between the two concentric cylinders, the external cylinder being fixed and the internal cylinder being in rotation at an angular velocity ω.

When the double emulsion is in the space between the two cylinders, the shear rate applied to the said emulsion is given by the following equation:

$$\gamma = \frac{R_i \omega}{(R_o - R_i)}$$

wherein:
ω is the angular velocity of the rotating internal cylinder;
$R_o$ is the internal radius of the fixed external cylinder; and
$R_i$ is the external radius of the internal rotating cylinder.

According to another embodiment, when the viscosity of the composition C3 is greater than 2000 mPa·s at 25° C., the step d) consists in applying to the emulsion (E2) a shear rate of less than 1000 s$^{-1}$.

According to this embodiment, the fragmentation step d) may be carried out by making use of any type of mixer usually used to form emulsions with a shear rate of less than 1000 s$^{-1}$, in which case the viscosity of the composition C3 is greater than 2000 mPa·s, that is to say, under conditions such as those described in the patent application FR 16 61787.

The geometric characteristics of the double droplets formed at the end of this step will dictate those of the future capsules.

According to this embodiment, in the step d), the emulsion (E2), constituted of polydisperse droplets dispersed in a continuous phase, is subjected to shear, for example in a mixer, at a low shear rate, that is to say less than 1000 s$^{-1}$.

According to this embodiment, the shear rate applied in the step d) is for example comprised between 10 s$^{-1}$ and 1000 s$^{-1}$.

Preferably, the shear rate applied in the step d) is strictly less than 1000 s$^{-1}$.

According to this embodiment, the droplets of emulsion (E2) can be efficiently fragmented into fine and monodisperse droplets of emulsion (E3) only if a high shear stress is applied thereto.

The shear stress σ applied to a droplet of emulsion (E2) is defined as the tangential force per unit surface area of droplet resulting from the macroscopic shear applied to the emulsion during agitation thereof during the step d).

The shear stress σ (expressed in Pa), the viscosity of the composition C3 η (expressed in Pa s) and the shear rate γ (expressed in $s^{-1}$) applied to the emulsion (E2) during agitation thereof during the course of step d) are linked by the following equation:

$$\sigma = \eta \gamma$$

Thus, according to this embodiment, the high viscosity of the composition C3 makes it possible to apply a very high shear stress to the droplets of emulsion (E2) in the mixer, even if the shear rate is low and the shear inhomogeneous.

In order to implement the step d) according to this embodiment, use may be made of any type of agitator usually used to form emulsions, such as, for example, a mechanical agitator with paddles, a static emulsifier, an ultrasonic homogeniser, a membrane homogeniser, a high pressure homogeniser, a colloid mill, a high shear disperser or a high speed homogeniser.

According to one preferred embodiment, use is made of a simple emulsifier such as a mechanical paddle agitator or a static emulsifier in order to implement the step d). Indeed, this is possible because this embodiment requires neither controlled shear nor shear force greater than 1000 $s^{-1}$.

Step e)

The step e) of the method of the invention consists of the crosslinking and therefore the formation of the enveloping shell of the solid microcapsules according to the invention.

This step makes it possible both to achieve the expected protection and retention performance of the capsules and to ensure the thermodynamic stability thereof, thereby definitively preventing any destabilisation mechanism such as coalescence or curing.

According to one embodiment, when the composition C2 comprises a photoinitiator, the step e) is a step of photopolymerisation consisting in exposing the emulsion (E3) to a light source that is capable of initiating the photopolymerisation of the composition C2, in particular to a UV light source emitting preferably in the wavelength range of between 100 nm and 400 nm, and this being in particular for a time period of less than or equal to 15 minutes.

According to this embodiment, the step e) consists in subjecting the emulsion (E3) to photopolymerisation, which will thus enable the photopolymerisation of the composition C2. This step will provide the ability to obtain microcapsules that encapsulate the volatil compound as defined here above.

According to one embodiment, the step e) consists in exposing the emulsion (E3) to a light source capable of initiating the photopolymerisation of the composition C2.

Preferably, the light source is a source of UV light.

According to one embodiment, the UV light source emits in the wavelength range of between 100 nm and 400 nm.

According to one embodiment, the emulsion (E3) is exposed to a light source for a period less than or equal to 15 minutes, and preferably for 5 to 10 minutes.

During the step e), the enveloping shell of the aforementioned double droplets, constituted of the photocrosslinkable composition C2, is cross-linked and thus converted into a viscoelastic polymeric enveloping shell, that encapsulates and protects the volatile compound(s) from being released in the absence of a mechanically triggered mechanism.

According to one other embodiment, when the composition C2 does not comprise a photoinitiator, the step e) is a polymerisation step, without exposure to a light source, with the duration of this step e) of polymerisation preferably being comprised between 8 hours and 100 hours and/or this step e) is carried out at a temperature comprised between 20° C. and 80° C.

According to this embodiment, the polymerisation is initiated for example by exposure to heat (thermal initiation), or simply by bringing about contact of the monomers, polymers and crosslinking agents with each other, or with a catalyst. The time of polymerisation is then generally greater than several hours.

Preferably, the step e) of polymerisation of the composition C2 is carried out for a time period of between 8 hours and 100 hours, at a temperature comprised between 20° C. and 80° C.

The composition obtained at the conclusion of step e), comprising of solid microcapsules dispersed in the composition C3, is ready for use and may be used without any additional step of post-treatment of the capsules being required.

The thickness of the enveloping shell of the microcapsules thus obtained is typically comprised between 10 nm and 2.5 μm, preferably between 100 nm and 1,000 nm.

According to one embodiment, the solid microcapsules obtained at the conclusion of the step e) are free of any surfactant, at the level of the interface between the solid enveloping shell and the external medium (or continuous phase) in particular represented by the composition C3.

The method of the invention has the advantage of not requiring a surfactant in any of the steps of forming the capsule shell. The method of the invention thus makes it possible to reduce the presence of additives which could modify the properties of the final product obtained after the release of the volatile compound.

The present invention also relates to a series (or set) of solid microcapsules, which it is possible to obtain in accordance with the method as defined here above, in which each microcapsule includes:

a core comprising of a composition C1 as defined here above; and a solid enveloping shell that completely encapsulates at its periphery the core, in which the mean diameter of the said microcapsules is comprised between 1 μm and 30 μm, the thickness of the rigid enveloping shell is comprised between 0.1 μm and 20 μm, and the standard deviation of the distribution of the diameter of microcapsules is less than 50%, in particular less than 25%, or less than 1% μm.

As indicated here above, the method of the invention makes it possible to obtain monodisperse particles. Also, the series of solid microcapsules mentioned here above is made up of a population of particles that are monodisperse in size. Thus, the standard deviation of the distribution of the diameter of microcapsules is less than 50%, in particular less than 25%, or less than 1 μm.

The distribution of size of the solid microcapsules can be measured by means of the light scattering technique using a Mastersizer 3000 (Malvern Instruments) equipped with a Hydro SV measurement cell.

According to one embodiment, the aforementioned solid microcapsules comprise a solid enveloping shell entirely composed of crosslinked polymer (obtained from the composition C2).

As indicated here above, the method of the invention makes it possible to obtain solid microcapsules. The present invention therefore also relates to solid microcapsules comprising of a core and a solid enveloping shell that completely encapsulates at its periphery the core, the core being a composition C1, and the said rigid enveloping shell being constituted of crosslinked polymer, with the diameter of the said capsule being comprised between 1 μm and 30 μm and the thickness of the rigid enveloping shell being comprised between 0.1 μm and 20 μm.

and wherein the composition C1 is:
either a composition C1a comprising a single hydrophobic solid particle,
or a composition C1b comprising a plurality of hydrophobic solid particles dispersed in a hydrophilic phase, said hydrophobic solid particles containing one or more lipophilic volatile compounds and one or more hydrophobic materials, solid at room temperature and liquid at a temperature above $T_m$, $T_m$ being between 30° C. and 80° C.

The present invention also relates to a composition comprising a series of solid microcapsules as defined here above.

According to a first variant embodiment, a composition according to the invention comprises solid microcapsules in which the composition C1 comprises several volatile lipophilic compounds, in particular perfuming agents, having different volatilities (or evaporation rates). Thus, during the application of a mechanical shear stress, for example represented by the application and spreading of such a composition on a keratinous material, in particular the skin, and in the case where the volatile lipophilic compounds are perfumes, the olfactory rendering is evolutionary in the sense that the perfuming agents will be felt in cascade in correlation with their respective evaporation rates.

According to another embodiment variant, the composition comprises at least one double population of solid microcapsules according to the invention which differ from each other at least at the level of the composition C1, in particular at the level of the perfuming agent. Thus, the olfactory note felt by the consumer results from the combination of the two perfuming agents. This embodiment is advantageous in that it notably makes it possible to stably and efficiently encapsulate incompatible volatile compounds when present within the same solution.

The compositions according to the invention may, in particular, be used in the cosmetics field.

They may comprise, in addition to the aforementioned ingredients, at least one physiologically acceptable medium.

The present invention therefore also relates to a cosmetic composition comprising a series of solid microcapsules as defined above, further comprising at least one physiologically acceptable medium.

By "physiologically acceptable medium" is meant a medium which is particularly suitable for the application of a composition of the invention to keratin materials, in particular the skin, the lips, the nails, the eyelashes or the eyebrows, and preferably the skin.

The physiologically acceptable medium is generally adapted to the nature of the medium to which the composition is to be applied, as well as to the appearance under which the composition is to be packaged.

According to one embodiment, the cosmetic compositions are used for the makeup and/or care of keratin materials, especially the skin.

The cosmetic compositions according to the invention may be skincare, sun protection, cleaning (makeup removal), hygiene or make-up products for the skin.

These compositions are therefore intended to be applied especially to the skin.

Thus, the present invention also relates to the non-therapeutic cosmetic use of a cosmetic composition mentioned above, as a makeup, hygiene, cleaning and/or care product for keratinous substances, in particular the skin.

According to one embodiment, the compositions of the invention are in the form of a foundation, a makeup remover, a facial and/or body and/or hair care, anti-age, sunscreen, oily skin care, a whitening care, a moisturizer, a BB cream, tinted cream or foundation, a face and/or body cleanser, a shower gel or a shampoo.

A care composition according to the invention may be, in particular, a solar composition, a care cream, a serum or a deodorant.

The compositions according to the invention may be in various forms, in particular in the form of cream, balm, lotion, serum, gel, gel-cream or mist.

The present invention also relates to a non-therapeutic method for the cosmetic treatment of a keratin material, comprising a step of applying to the keratinous material at least one layer of a cosmetic composition as defined above.

In particular, the present invention relates to a non-therapeutic method for cosmetic treatment of the skin, comprising a step of applying to the skin at least one layer of a cosmetic composition as defined above.

The present invention also relates to a method for releasing a volatile compound, comprising a step of applying a mechanical shear stress to a composition comprising a series of solid microcapsules as defined above.

The expressions "comprised between . . . and . . . ", "ranging from . . . to . . . " and "from . . . to . . . " are to be understood as inclusive of limits, unless otherwise specified.

The following examples are provided by way of illustrating the present invention without limiting the scope thereof.

EXAMPLES

Example 1: Manufacture of Solid Capsules According to the Invention

A mechanical agitator (Ika Eurostar 20) equipped with a deflocculating type propeller stirrer is used to carry out all the stirring/agitation steps.
Step a): Creation of the Core of the Capsules (Dispersion of Particles—Composition C1b)

|  |  | Weight (g) | % |
| --- | --- | --- | --- |
| Composition C1a | Fragrance | 21.6 | 54 |
|  | Saturated triglyceride wax (Suppocire DM wax, Gattefosse) | 2.4 | 6 |
| Composition B | Dispersant (Tween 80, Sigma Aldrich) | 0.8 | 2 |
|  | Deionized water | 15.2 | 38 |
|  | Total | 40 | 100 |

The composition C1a is placed in a bath thermostated at 35° C. and stirred at 500 rpm until complete dissolution of the wax. Composition B is placed in a bath thermostated at 35° C. and stirred at 200 rpm until complete homogenization. The composition C1a is then added to the composition B dropwise with stirring at 2000 rpm, still at 35° C. The mixture is stirred at 2000 rpm for 5 minutes and then sonicated (Vibra-cell 75042, Sonics) for 20 minutes (pulse 5 s/2 s) at 30% amplitude. If the temperature exceeds 35° C. during sonication, the mixture is cooled using ice.

After cooling, 1.2 g of gelling agent (modified polyethylene glycol, Aculyn 44N, Dow) are added to the mixture with stirring at 500 rpm until gelation. Alternatively, Aculyn 44N can be replaced by a carbomer (Tego Carbomer 340 FD). The composition C1b is thus obtained.

Step b): Preparation of the First Emulsion (E1)

|  |  | Weight (g) | % Total |
|---|---|---|---|
|  | Composition C1b | 4 | 40 |
|  | Composition C2 | 6 | 60 |
| Composition C2 | CN2203 (Polyester acrylate oligomer, Sartomer) | 5.72 |  |
|  | CN381 (modified amine polyether oligomer, Sartomer) | 0.1 |  |
|  | Darocur 1173 (photoinitiator, BASF) | 0.18 |  |
|  | Total | 10 | 100 |

The composition C1 is added dropwise to the composition C2 with stirring at 2000 rpm, at a temperature $T_b$=20° C. The first emulsion (E1) is thus obtained.

Step c): Preparation of the Second Emulsion (E2)

|  |  | Weight (g) | % total |
|---|---|---|---|
|  | First emulsion | 5 | 5 |
| Composition C3 | Sodium alginate (Sigma Aldrich) | 9.5 | 9.5 |
|  | Deionized water | 85.5 | 85.5 |
|  | Total | 100 | 100 |

The composition C3 is placed under agitation at 1000 rpm until complete homogenization is obtained and then allowed to stand for a period of one hour at ambient temperature. The first emulsion (E1) is then added to the composition C3 under stirring at 1000 rpm, at a temperature $T_c$=20° C. The second emulsion (E2) is thus obtained.

Step d): Size Refinement of the Second Emulsion

The second polydisperse emulsion obtained in the preceding step is agitated at 1000 rpm for a period of 10 minutes, at a temperature $T_d$=20° C. A monodisperse emulsion (E3) is thus obtained.

Step e): Cross-Linking of the Enveloping Shell of the Capsules

The second monodisperse emulsion (E3) obtained in the previous step is irradiated for a period of 15 minutes by using a UV light source (Dymax LightBox ECE 2000) having a maximum luminous intensity of 0.1 W/cm$^2$ at a wavelength of 365 nm.

The solid microcapsules according to example 1 present a good size distribution, that is to say, an average size of 7.9 μm and a standard deviation of 3.8 μm that is 48%.

Furthermore, the quality of encapsulation of the volatile lipophilic compound, namely the perfuming agent, with the microcapsules according to Example 1 was studied by incubation at 50° C. for 30 days with a suspension of the microcapsules of Example 1 in a carbomer solution (Tego carbomer 750FD, Evonik) at 0.3%.

There is no change in color or smell emanation, especially the encapsulated perfume agent, even after stirring. It is also noted that the viscosity of the suspension does not undergo a significant decrease, indicating the absence of leakage of the perfuming agent outside the capsules where it would cause the coagulation of the carbomer causing a drop in viscosity.

The solid microcapsules according to Example 1 thus prove to be particularly suitable for effectively encapsulating a volatile lipophilic compound, in particular a perfuming agent.

Example 2: Manufacture of Solid Capsules According to the Invention

Example 2 differs from Example 1 only in the nature of composition C2, as described below. All the other parameters, protocols, steps, compositions described in example 1 remain identical.

|  | Raw materials | % for C2 | Ratio C1-C2 |
|---|---|---|---|
|  | Composition C1b | — | 4 |
| Composition C2 | CN 981 (aliphatic polyester/ether urethane acrylate oligomer, Sartomer) | 87 | 6 |
|  | SR238 (1,6-hexanediol diacrylate, Sartomer) | 10 |  |
|  | Darocur 1173 (2-Hydroxy-2-methyl-1-phenyl-propan-1-one, photoinitiator, BASF) | 3 |  |
|  | Total | 100 | 10 |

Example 3: Manufacture of Solid Capsules According to the Invention

Example 3 differs from Examples 1 and 2 only in the nature of composition C3, as described below. All the other parameters, protocols, steps, compositions described in example 1 remain identical.

Step c): Preparation of the Second Emulsion (E2)

|  |  | Weight (g) | % total |
|---|---|---|---|
| First emulsion (E1) |  | 5 | 5 |
| Composition C3 | Modified polyethylene glycol gelling agent (Aculyn 44N, Dow) | 2.85 | 2.85 |
|  | Deionized water | 92.15 | 92.15 |
|  | Total | 100 | 100 |

The invention claimed is:

1. A method for preparing solid microcapsules comprising the following steps:
   a) preparation of a composition C1, which is either a composition C1a, comprising a single hydrophobic solid particle, or a composition C1b comprising a plurality of hydrophobic solid particles dispersed in a hydrophilic phase, the hydrophobic solid particle(s) containing one or more lipophilic volatile compounds and one or more hydrophobic materials, solid at room temperature and liquid at a temperature above $T_m$,
   b) addition, with stirring, of the composition C1 in a polymeric composition C2 at a temperature $T_b$, the compositions C1 and C2 being immiscible with one another, the temperature $T_b$ being greater than $T_m$ when the composition C1 is a composition C1a and the temperature $T_b$ being less than $T_m$ when the composition C1 is a composition C1b, the composition C2 comprising at least one monomer or polymer, at least one crosslinking agent, and optionally at least one (photo)initiator or crosslinking catalyst, the viscosity of the composition C2 being between 500 mPa·s and 100 000 mPa·s at 25° C., and preferably being greater than the viscosity of the composition C1, whereby an emulsion (E1) comprising drops of composition C1a or C1b dispersed in composition C2 is obtained;

c) addition, with stirring, of the emulsion (E1) in a composition C3 at a temperature $T_c$, the compositions C2 and C3 not being miscible with each other, the temperature $T_c$ being greater than $T_m$ when the emulsion (E1) comprises drops of composition C1a dispersed in composition C2 and the temperature $T_c$ being less than $T_m$ when the emulsion (E1) comprises drops of composition C1b dispersed in the composition C2, the viscosity of the composition C3 being between 500 mPa·s and 100 000 mPa·s at 25° C., and preferably being greater than the viscosity of the emulsion (E1), whereby a double emulsion (E2) comprising drops dispersed in the composition C3 is obtained;

d) applying shear to the emulsion (E2) at a temperature $T_d$, the temperature $T_d$ being greater than $T_m$ when the composition C1 of step a) is a composition C1a and the temperature $T_d$ being less than $T_m$ when the composition C1 of step a) is a composition C1b, whereby a double emulsion (E3) is obtained comprising controlled size drops dispersed in the composition C3; and e) polymerization of the composition C2, whereby solid microcapsules dispersed in the composition C3 are obtained.

2. The method according to claim 1, wherein the hydrophobic material(s) is/are chosen from waxes, butters or pasty fatty substances, and mixtures thereof.

3. The method according to claim 1, wherein the volatile lipophilic compounds are chosen from perfuming agents, flavonoids, polyunsaturated fatty acids, and mixtures thereof.

4. The method according to claim 1, wherein the hydrophilic phase of C1b comprises at least one dispersing agent and at least one gelling agent.

5. The method according to claim 4, wherein the gelling agent is selected from branched polymers, polymers of molecular weight greater than 5000 g/mol$^{-1}$, cellulose derivatives, polyacrylates, polyurethanes and their derivatives, polyethers and their derivatives, polyacrylamides, polyvinylpyrrolidone (PVP) and its derivatives, polyvinyl alcohol (PVA) and its derivatives, poly(ethylene) glycol), poly(propylene glycol) and their derivatives, polysaccharides, protein derivatives, fatty acid salts, glycerol derivatives, glycoluril derivatives, and mixtures thereof.

6. The method according to claim 4, wherein the dispersing agent is selected from the group consisting of surfactants; polyacrylates; sugar/polysaccharide esters and fatty acid(s); polyamides; polyethers and polyesters of silicone; ethoxylated alcohols; and mixtures thereof.

7. The method according to claim 1, wherein, when the composition C1 is a composition C1a, step a) comprises a step of heating the hydrophobic material or materials at a temperature above $T_m$, followed by a step of adding the lipophilic volatile compound(s), and a step of mixing the assembly at a temperature greater than $T_m$.

8. The method according to claim 1, wherein, when the composition C1 is a C1b composition, step a) further comprises a step of dispersing the composition C1a in the hydrophilic phase, followed by a cooling step of the dispersion thus obtained at a temperature below $T_m$, whereby hydrophobic solid particles dispersed in said hydrophilic phase are obtained.

9. The method according to claim 1, wherein the step d) consists in applying a homogeneous controlled shear to the emulsion (E2), with the said shear rate applied between 1000 s$^{-1}$ and 100,000 s$^{-1}$.

10. The method according to claim 1, wherein the viscosity of the composition is greater than 2000 mPa·s at 25° C., the step d) consists in applying to the emulsion (E2) a shear rate of less than 1000 s$^{-1}$.

11. The method according to claim 1, in which, when the composition C2 comprises a photoinitiator, the step e) is a step of photopolymerisation consisting in exposing the emulsion (E3) to a light source that is capable of initiating the photopolymerisation of the composition C2.

12. The method according to claim 1, in which, when the composition C2 does not comprise a photoinitiator, the step e) is a polymerisation step, without exposure to a light source.

13. A series of solid microcapsules, susceptible to be obtained with the method according to claim 1, in which each microcapsule includes:
  a core comprising of a composition C1 as defined according to any one of claims 1 to 8; and
  a solid enveloping shell that completely encapsulates at its periphery the core; in which the mean diameter of the said microcapsules is comprised between 1 µm and 30 µm, the thickness of the rigid enveloping shell is comprised between 0.1 µm and 20 µm and the standard deviation of the distribution of the diameter of microcapsules is less than 50% or less than 1 µm.

14. A composition comprising a series of solid microcapsules according to claim 13.

15. A cosmetic composition comprising a series of solid microcapsules according to claim 13, further comprising at least one physiologically acceptable medium.

16. A method of releasing a volatile compound, comprising a step of applying mechanical shear stress to a composition comprising a series of solid microcapsules according to claim 14.

17. The method according to claim 2, wherein the volatile lipophilic compounds are chosen from perfuming agents, flavonoids, polyunsaturated fatty acids, and mixtures thereof.

18. A method of releasing a volatile compound, comprising a step of applying mechanical shear stress to a composition comprising a series of solid microcapsules according to claim 15.

* * * * *